United States Patent
Reddy et al.

(10) Patent No.: US 8,532,792 B2
(45) Date of Patent: Sep. 10, 2013

(54) HELIX RETRACTION ASSIST MECHANISM

(75) Inventors: G. Shantanu Reddy, Minneapolis, MN (US); Ryan Kleve, Maple Grove, MN (US); Adam J. Rivard, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 236 days.

(21) Appl. No.: 13/110,351

(22) Filed: May 18, 2011

(65) Prior Publication Data

US 2012/0004667 A1 Jan. 5, 2012

Related U.S. Application Data (60) Provisional application No. 61/360,163, filed on Jun. 30, 2010.

(51) Int. Cl.
 *A61N 1/00* (2006.01)
 *A61B 19/00* (2006.01)

(52) U.S. Cl.
 USPC .......................................... 607/127; 606/129

(58) Field of Classification Search
 USPC .................. 606/129; 607/122, 126, 127, 115
 See application file for complete search history.

(56) References Cited

U.S. PATENT DOCUMENTS

| | | | |
|---|---|---|---|
| 4,217,913 A | 8/1980 | Dutcher | |
| 4,924,881 A | 5/1990 | Brewer | |
| 4,972,848 A | 11/1990 | DiDomenico et al. | |
| 5,003,992 A | 4/1991 | Holleman et al. | |
| 5,056,515 A | 10/1991 | Abel | |
| 5,076,285 A | 12/1991 | Hess et al. | |
| 5,259,395 A | 11/1993 | Li | |
| 5,360,441 A | 11/1994 | Otten | |
| 5,387,233 A * | 2/1995 | Alferness et al. | 607/126 |
| 5,522,875 A | 6/1996 | Gates et al. | |
| 6,033,414 A | 3/2000 | Tockman et al. | |
| 6,078,840 A | 6/2000 | Stokes | |
| 6,097,986 A | 8/2000 | Janke et al. | |
| 6,459,937 B1 * | 10/2002 | Morgan et al. | 607/126 |
| 6,611,710 B2 | 8/2003 | Gomperz et al. | |
| 6,763,270 B1 | 7/2004 | Gomperz et al. | |
| 7,092,766 B1 | 8/2006 | Salys et al. | |
| 7,981,121 B2 * | 7/2011 | Stegfeldt et al. | 606/129 |
| 2002/0065543 A1 | 5/2002 | Gomperz et al. | |
| 2004/0068299 A1 | 4/2004 | Laske et al. | |
| 2005/0085885 A1 | 4/2005 | Janke et al. | |
| 2006/0089698 A1 | 4/2006 | Sundberg et al. | |

(Continued)

FOREIGN PATENT DOCUMENTS

| | | |
|---|---|---|
| WO | 0040293 | 7/2000 |
| WO | 2007123443 | 11/2007 |

OTHER PUBLICATIONS

International Search Report and Written Opinion issued in PCT/US2011/036942, mailed Dec. 19, 2011, 19 pages.

(Continued)

*Primary Examiner* — Tuan V Nguyen
(74) *Attorney, Agent, or Firm* — Faegre Baker Daniels LLP (57) ABSTRACT

An active fixation implantable medical lead may include an electrode base that is configured to accommodate an extraction stylet that may be used if the fixation helix is not otherwise easily retracted. An extraction tool may be used in combination with the extraction stylet in extraction techniques designed for retraction of a fixation helix.

11 Claims, 6 Drawing Sheets

(56) References Cited

U.S. PATENT DOCUMENTS

2007/0123967 A1    5/2007    Barlov et al.
2007/0299493 A1    12/2007    Osypka
2010/0030312 A1    2/2010    Shen

OTHER PUBLICATIONS

Invitation to Pay Additional Fees issued in PCT/US2011/036942, mailed Aug. 25, 2011, 8 pages.

* cited by examiner

HELIX RETRACTION ASSIST MECHANISM

CROSS-REFERENCE TO RELATED APPLICATION

This application claims the benefit under 35 U.S.C. §119 (e) to U.S. Provisional Patent Application No. 61/360,163, filed on Jun. 30, 2010, entitled "HELIX RETRACTION ASSIST MECHANISM," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is an implantable lead assembly that includes a flexible lead body extending between a proximal end and a distal end. A connector assembly including a terminal pin rotatable relative to the lead body is secured to the proximal end for coupling the lead to an implantable medical device. A coil conductor is disposed longitudinally within the lead body, the coil conductor is rotatable relative to the lead body and is coupled to the terminal pin, the coil conductor defining a lumen extending through the coil conductor. An electrode base having a proximal end and a distal end is rotatably disposed within the lead body. The proximal end is connected to the coil conductor and includes an extraction aperture aligned with the coil conductor lumen. A helical electrode is fixedly secured to the electrode base, the electrode base being rotatably engaged with the terminal pin via the coil conductor such that rotation of the terminal pin in a first direction causes the electrode base to rotate in a first direction that extends the helical electrode and rotation of the terminal pin in a second direction causes the electrode base to rotate in a second direction that retracts the helical electrode. The extraction aperture is configured to engage a distal end of an extraction stylet that is disposable within the coil conductor lumen. The extraction stylet provides additional torque for retracting the helical electrode when rotation of the terminal pin in the second direction is not sufficient to retract the helical electrode.

In Example 2, the implantable lead assembly of Example 1 in which the extraction aperture includes an elongate slot.

In Example 3, the implantable lead assembly of Example 2 in which the distal end of the extraction stylet includes an engagement portion configured to engage the elongate slot.

In Example 4, the implantable lead assembly of any of Examples 1-3 in which the coil conductor has a handedness that enables the coil conductor to decrease in diameter and thus engage the extraction stylet in response to the terminal pin being rotated a predetermined number of turns in the second direction.

In Example 5, the implantable lead assembly of Example 4 in which the predetermined number of turns is in the range of about 5 to about 25 turns.

In Example 6, the implantable lead assembly of any of Examples 1-5, further including a lead extraction tool that is engageable with the lead body and selectively securable to the lead body, the lead extraction tool being configured to selectively secure the extraction stylet to the tool and/or the terminal pin to the tool.

In Example 7, the implantable lead assembly of Example 6 in which the lead extraction tool is configured for rotating the terminal pin relative to the lead body.

In Example 8, the implantable lead assembly of Example 6 or Example 7 in which the lead extraction tool is configured for rotating the extraction stylet relative to the lead body.

In Example 9, the implantable lead assembly of any of Examples 6-8 in which the lead extraction tool is configured for simultaneously rotating the terminal pin and the extraction stylet relative to the lead body.

Example 10 is an extraction tool assembly for use with an implantable active fixation lead that has a proximal end, a terminal pin extending from the proximal end and a stylet lumen extending through the terminal pin. The extraction tool assembly includes an extraction stylet and an extraction tool. The extraction tool includes a main body having a proximal section, a distal section and an intermediate section. A lumen extends through the main body and is configured to accommodate an extraction stylet. A funnel within the proximal section is configured to provide stylet access to the lumen extending through the main body. An opening within the distal section is configured to frictionally engage a proximal end of the implantable lead, the opening aligned with the lumen extending through the main body. A lead locking device is disposed within the distal section and is configured to releasably secure the proximal end of the implantable lead relative to the extraction tool. A terminal pin locking device is disposed within the intermediate section and is configured to releasably secure the terminal pin relative to the extraction tool. A stylet locking device is disposed within the proximal section and is configured to releasably secure the extraction stylet relative to the extraction tool.

In Example 11, the extraction tool assembly of Example 10 in which the lead locking device is threadedly engaged with the extraction tool and includes a thumbwheel for rotating the lead locking device between a retracted position in which the lead is movable relative to the extraction tool and an extended position in which the lead is held secure relative to the extraction tool.

In Example 12, the extraction tool assembly of Example 10 or Example 11 in which the terminal pin locking device is threadedly engaged with the extraction tool and includes a thumbwheel for rotating the terminal pin locking device between a retracted position in which the terminal pin is rotatable relative to the extraction tool and an extended position in which the terminal pin is held secure relative to the extraction tool.

In Example 13, the extraction tool assembly of any of Examples 10-12 in which the stylet locking device is threadedly engaged with the extraction tool and includes a thumbwheel for rotating the stylet locking device between a retracted position in which the stylet is movable relative to the extraction tool and an extended position in which the stylet is held secure relative to the extraction tool.

In Example 14, the extraction tool assembly of any of Examples 10-13 in which the extraction stylet includes a distal end that is configured to engage an electrode base within the implantable active fixation lead.

In Example 15, the extraction tool assembly of Example 14 in which the electrode base includes an extraction slot disposed within a proximal end of the electrode base, and the distal end of the extraction stylet includes a widened blade portion complementary to the extraction slot.

Example 16 is a method of extracting an active fixation lead having a proximal end, a coil conductor, a terminal pin secured to a proximal end of the coil conductor, an electrode base secured to a distal end of the coil conductor, the electrode base including an extraction slot, and a fixation helix secured to the electrode base, and a lumen extending through the coil conductor to accommodate an extraction stylet. An extraction tool that is configured to releasably and interchangeably secure the terminal pin, the extraction stylet and/or the proximal end of the lead relative to the extraction tool is disposed over the proximal end of the lead. An extraction stylet is inserted through the extraction tool and into engagement with the extraction slot. The terminal pin is secured relative to the extraction tool, and the extraction tool is then rotated a number of turns sufficient to cause the coil conductor to wind down onto the extraction stylet. The proximal end of the lead is secured relative to the extraction tool and the extraction stylet is then secured relative to the extraction tool. The proximal end of the lead is released relative to the extraction tool, and the extraction tool is then rotated an additional number of turns to retract the fixation helix.

In Example 17, the method of Example 16 further including a subsequent step of securing the proximal end of the lead relative to the extraction tool in order to hold any torque previously applied to the extraction stylet and coil conductor.

In Example 18, the method of Example 17 further including a subsequent step of clipping the extraction tool to a surgical drape to see if the held torque will loosen the fixation helix.

In Example 19, the method of any of Examples 16-18 in which rotating the extraction tool a number of turns sufficient to cause the coil conductor to wind down onto the extraction stylet includes rotating the extraction tool about 5 to about 25 turns.

In Example 20, the method of any of Examples 16-19 in which rotating the extraction tool an additional number of turns to retract the fixation helix includes rotating the extraction tool about 3 to about 10 turns.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
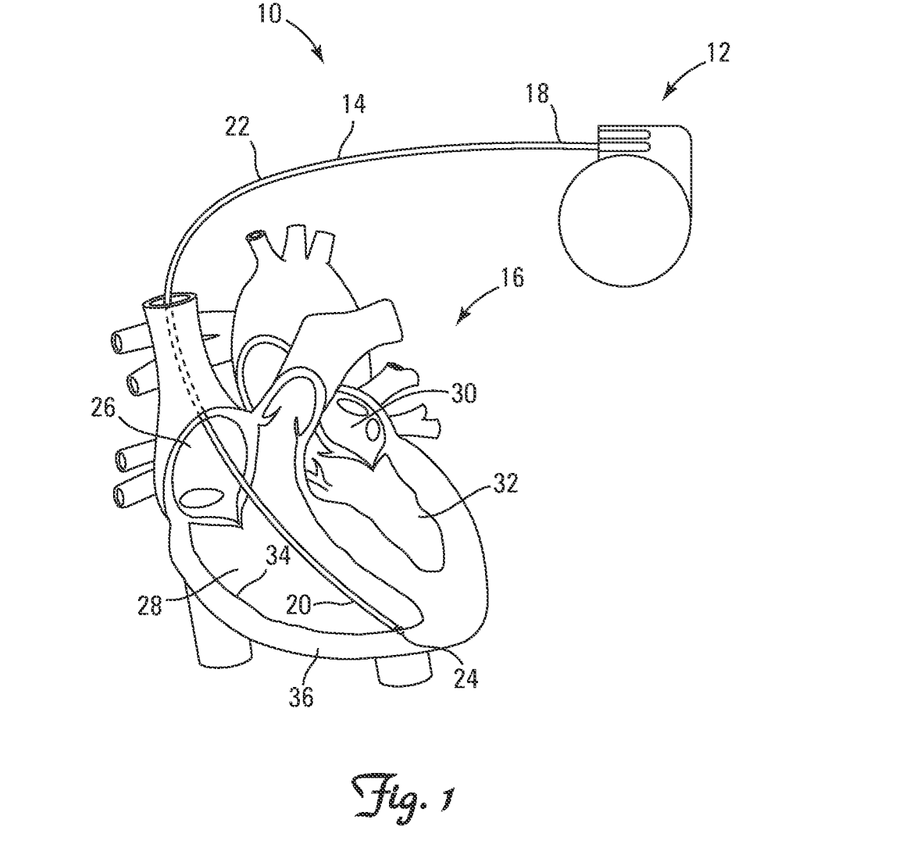
FIG. 1 is a combined cutaway and perspective view of an implantable medical device and lead in accordance with an embodiment of the present invention.

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes an extendable/retractable fixation helix 24, which as will be discussed in greater detail below locates and/or secures the distal region 20 within the heart 16.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 and/or to apply a stimulating pulse to the right ventricle 28. In other embodiments, the fixation helix 24 is not electrically active. Rather, in some embodiments, other components of the lead 14 are electrically active.

Figure 2:
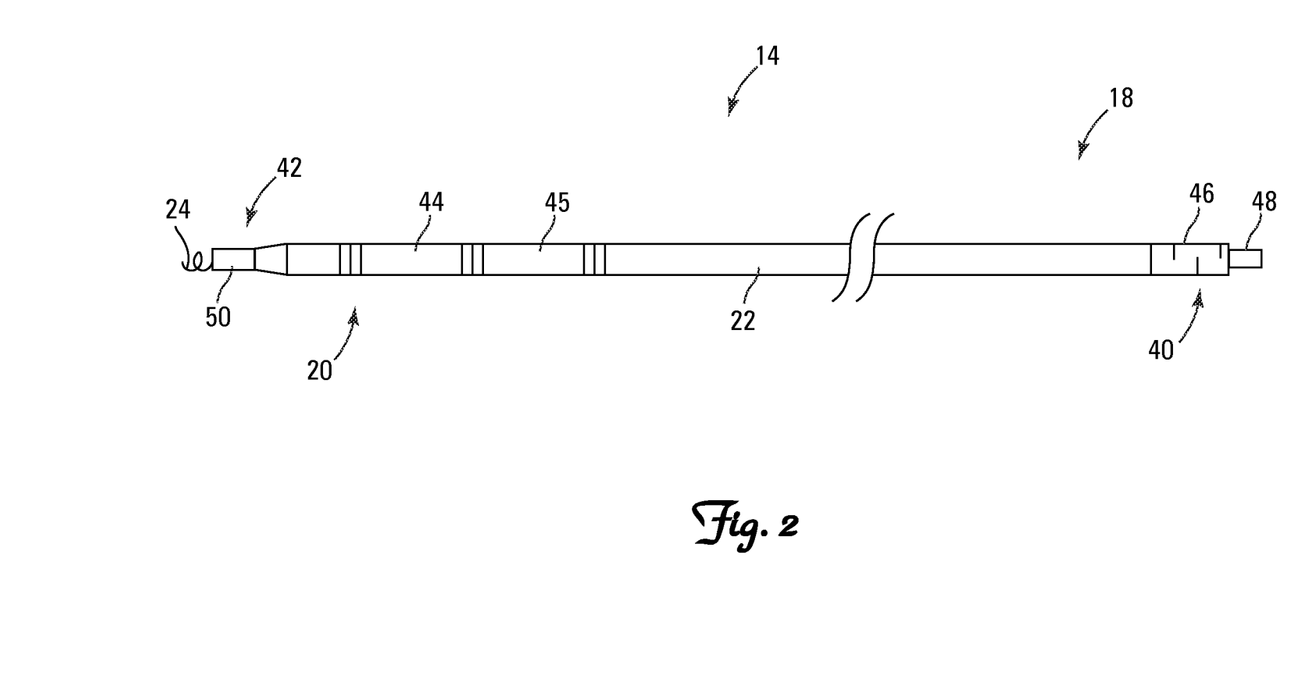
FIG. 2 is a side elevation view of the lead of FIG. 1.

FIG. 2 is an isometric illustration of the lead 14 according to one embodiment. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally within the lead body 22 and which is rotatable relative to the lead body 22 such that rotating the terminal pin 48 (relative to the lead body 22) causes the conductor member to rotate within the lead body 22 as well.

In some embodiments, the terminal pin 48 includes an aperture extending therethrough, and the conductor member defines a longitudinal lumen in communication with the aperture. When present, the aperture and/or conductor lumen are configured to accommodate a guide wire or an insertion stylet for delivery of the lead 14. In some embodiments, as will be described in greater detail hereinafter, the aperture and/or conductor lumen may accommodate an extraction stylet.

The distal assembly 42 includes a housing 50, within which the fixation helix 24 is at least partially disposed. In some embodiments, as will be described, the housing 50 includes or accommodates a mechanism that enables the fixation helix 24 to move distally and proximally relative to the housing 50. In some embodiments, the housing 50 may accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, tungsten, tantalum, iridium, platinum, titanium, palladium, stainless steel, as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

Figure 3:
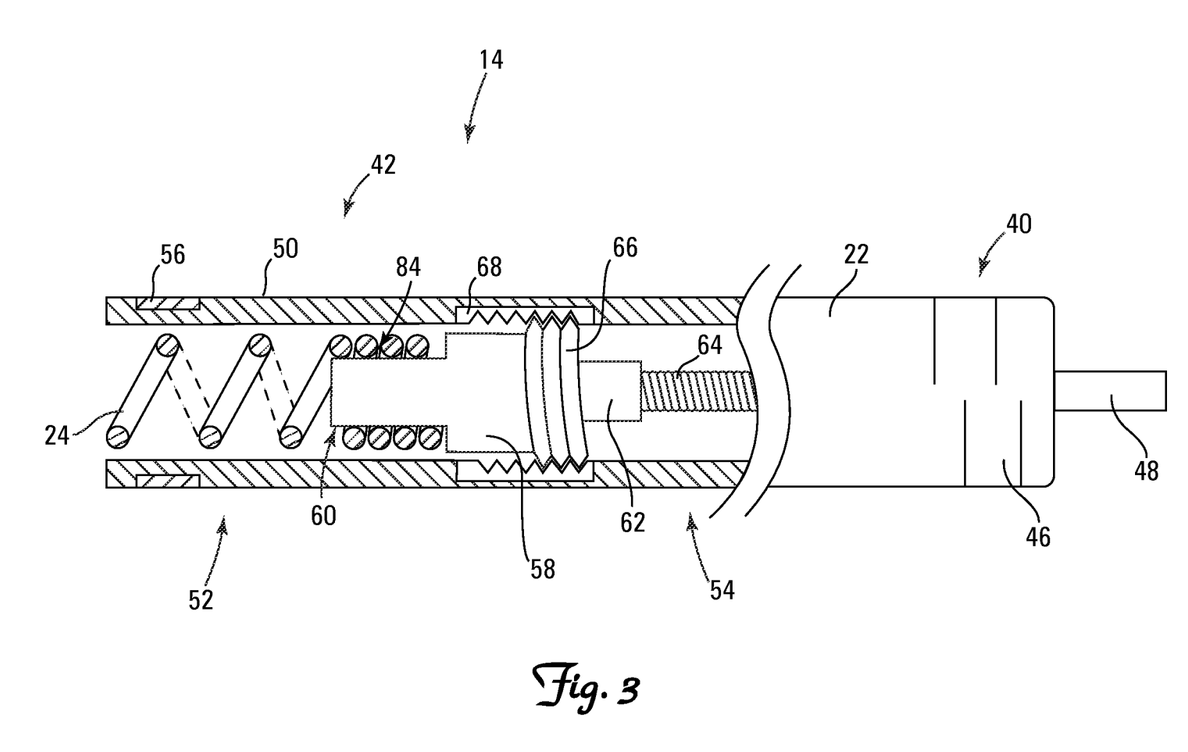
FIG. 3 is a partial cross-sectional view of the lead of FIG. 1.

FIG. 3 illustrates an embodiment of a lead including a distal assembly in accordance with one embodiment of the present invention. In FIG. 3, the fixation helix 24 is illustrated in a retracted position. In the illustrated embodiment, the fixation helix 24 is electrically active so as to be operable as a pace/sense electrode.

As shown in FIG. 3, the housing 50 includes a distal region 52 and a proximal region 54. The housing 50 is, in general, relatively rigid or semi-rigid. In some embodiments, the housing 50 is made of an electrically conductive material such as Elgiloy, MP35N, tungsten, tantalum, iridium, platinum, titanium, palladium, stainless steel, as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 56.

As shown, the distal assembly 42 includes an electrode base 58. In some embodiments, the electrode base 58 is made of an electrically conductive material such as Elgiloy, MP35N, tungsten, tantalum, iridium, platinum, titanium, palladium, stainless steel, as well as alloys of any of these materials. In some embodiments, the electrode base 58 is made of a non-electrically conductive material such as PES (polyethersulfone), polyurethane-based thermoplastics, ceramics, polypropylene and PEEK (polyetheretherketone).

In some embodiments, the electrode base 58 is configured to move longitudinally and/or rotationally with respect to the housing 50. As illustrated, the electrode base 58 includes a distal portion 60 and a proximal portion 62. As shown, the fixation helix 24 is connected to the distal portion 60 of the electrode base 58. In some embodiments, as illustrated, the distal portion 60 may have a relatively smaller diameter (relative to at least part of the central portion 64) that is configured to accommodate the fixation helix 24. In some embodiments, the proximal portion 62 of the electrode base 58 may be configured to accommodate a seal (not illustrated).

A conductor coil 64 is secured to the proximal portion 62 of the electrode base 58, and extends proximally through the lead body 22 to the connector assembly 40. In some embodiments, the conductor coil 64 includes or is otherwise formed from a metallic coil. In some embodiments, the conductor coil 64 may be configured to have a handedness, either a right handed orientation or a left handed orientation, that may be chosen to provide the conductor coil 64 with a desired tendency to either wind down or alternatively to unwind when rotated in a particular direction.

In this, handedness may be defined via a coil winding direction relative to the lead. A right handed orientation may be defined as a winding that proceeds from left to right relative to a proximal to distal view of the conductor coil 64. Conversely, a left handed orientation may be defined as a winding that proceeds from right to left relative to a proximal to distal view of the conductor coil 64.

The electrode base 58 provides an electrical connection between the conductor coil 64 and the fixation helix 24. In some embodiments, as will be described with respect to FIG. 4, the conductor coil 64 may extend into the proximal portion 62 of the electrode base. In some embodiments, the conductor coil 64 is welded or soldered to the proximal portion 62 of the electrode base 58.

In the connector assembly 40, the conductor coil 64 is coupled to the terminal pin 48 such that rotation of the terminal pin 48 causes the conductor coil 64 to rotate. As the conductor member 64 rotates, the electrode base 58 and the fixation helix 24 will also rotate. In some embodiments, the fixation helix 24 is rotated via a stylet that is inserted through an aperture that may be formed within the terminal pin 48 (FIG. 2).

In some embodiments, as illustrated, the electrode base 58 includes a threaded portion 66 that interacts with a corresponding threaded portion 68 secured within the housing 50. It will be appreciated that relative rotation between the threaded portion 66 and the threaded portion 68 will cause the electrode base 58 to translate or move axially relative to the housing 50. The threaded portion 66 and the threaded portion 68 may, in combination, be configured to have a left hand thread or a right hand thread. For example, the threaded portion 66 and the threaded portion 68 may be configured such that rotating the terminal pin 48 in a clockwise fashion will cause the electrode base 58 and the fixation helix 24 to move outwards towards an extended position while counter clockwise rotation of the terminal pin 48 may retract the electrode base 58 and the fixation helix 24.

The particular arrangement illustrated in FIG. 3 facilitating extension and retraction of the fixation helix 24 is exemplary only. In other words, any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Provisional Patent Application 61/181,954, the disclosure of which is incorporated by reference herein in its entirety. In other embodiments, a different arrangement for extending and retracting the fixation helix 24 is utilized.

As discussed, the lead 14 is configured such that rotating the terminal pin 48 in one direction extends the fixation helix 24 relative to the housing 50 while rotating the terminal pin 48 in a second, opposing, direction withdraws the fixation helix 24 relative to the housing 50. In some embodiments, tissue ingrowth in and near the fixation helix 24 may render extraction somewhat more problematic. In some embodiments, extraction of the lead 14, by withdrawing the fixation helix 24, may be negatively impacted if the conductor coil 64 is broken. Thus, in some embodiments, the lead 14 may be configured to accommodate new extraction techniques.

Figure 4:
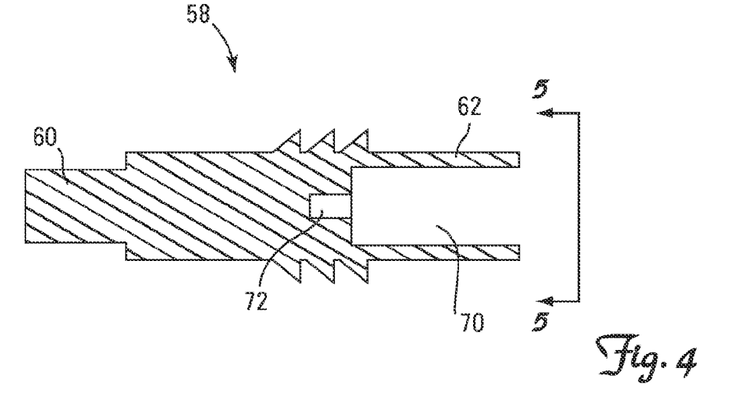
FIG. 4 is an axial cross-sectional view of an electrode base in accordance with an embodiment of the present invention.
Figure 5:
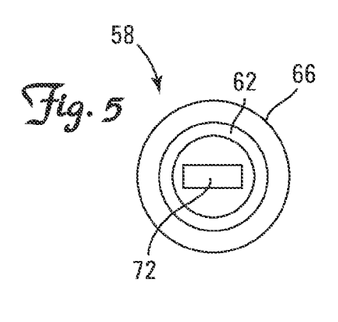
FIG. 5 is a radial cross-sectional view of the electrode base of FIG. 4.

In some embodiments, the electrode base 58 may be configured to accommodate and interact with an extraction stylet. As seen in FIG. 4, the proximal portion 62 of the electrode base 58 may include an elongate aperture 70 that is configured to accommodate a proximal end of the conductor coil 64 therein. An extraction slot 72 is formed at the bottom of the elongate aperture 70 and is aligned with the lumen, previously discussed, extending through the conductor coil 64. FIG. 5 is a radial cross-section, showing the extraction aperture 72. While the extraction aperture 72 is illustrated as a rectangular aperture, in some embodiments the extraction aperture 72 may have other shapes and configurations. For example, the extraction aperture 72 may be configured to accommodate an extraction stylet having a hex head configuration.

Figure 6:
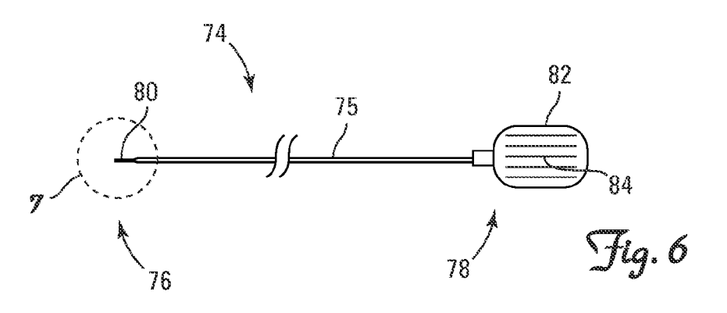
FIG. 6 is a side elevation view of an extraction stylet in accordance with an embodiment of the present invention.
Figure 7:
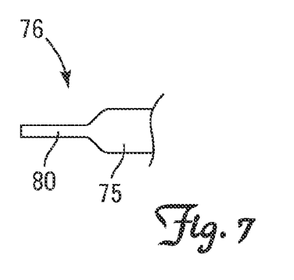
FIG. 7 is an enlarged view of a portion of the extraction stylet of FIG. 6.

FIG. 6 is a side elevation view of an extraction stylet 74 having a distal end 76 and a proximal end 78. The distal end 76 is configured to interact with the extraction aperture 72. In the illustrated embodiment, the distal end 76 is formed as a widened blade 80, although other configurations are possible, depending on the shape and configuration of the extraction aperture 72. The proximal end 78 includes a handle 82 that may, for example, include a knurled surface 84 that renders the handle 82 easier to manipulate. The extraction stylet 74 may be sized so that it is at least as long as the lead 14 and has an outer diameter along its shaft 75 that is as close as possible to an inner diameter of the lumen extending through the conductor coil 64.

In some embodiments, the extraction stylet 74 may include a surface treatment or coating that, as will be described, helps the extraction stylet 74 interact with the conductor coil 64. In some embodiments, at least portions of the extraction stylet 74 may undergo a surface treatment such as a surface roughening treatment to increase potential frictional forces between the conductor coil 64 and the extraction style 74. In some embodiments, at least portions of the extraction coil 74 may include a coating that increases frictional forces, particularly when the conductor coil 64 is wound down into contact with the extraction stylet 74.

In some embodiments, particularly if rotation of the terminal pin 48 does not readily retract the fixation helix 24, a user may extend the extraction stylet 74 through the terminal pin 48, through the conductor coil 64 and into the extraction aperture 72 formed within the proximal portion 62 of the electrode base 58. By doing so, the user may exert additional torque on the electrode base 58. In some situations, this alone may be sufficient to break the fixation helix 24 loose from any surrounding tissue ingrowth and thus withdraw the fixation helix 24 into the housing 50 so that the lead 14 may be more easily removed from the heart 16.

Figure 8:
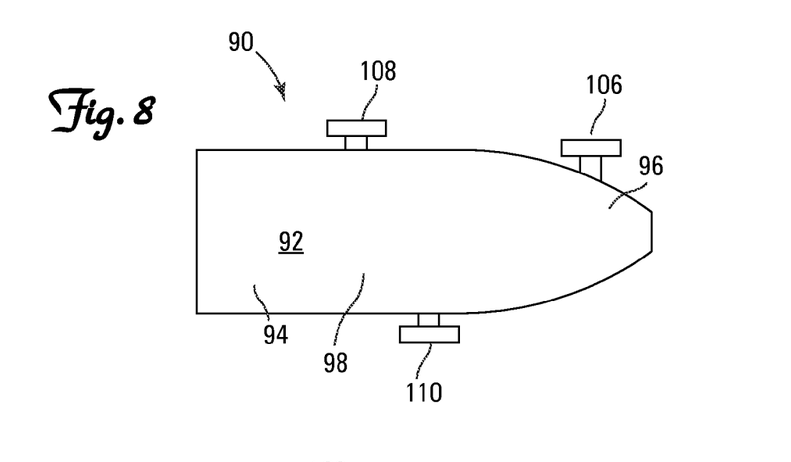
FIG. 8 is a side elevation view of an extraction tool in accordance with an embodiment of the present invention.
Figure 9:
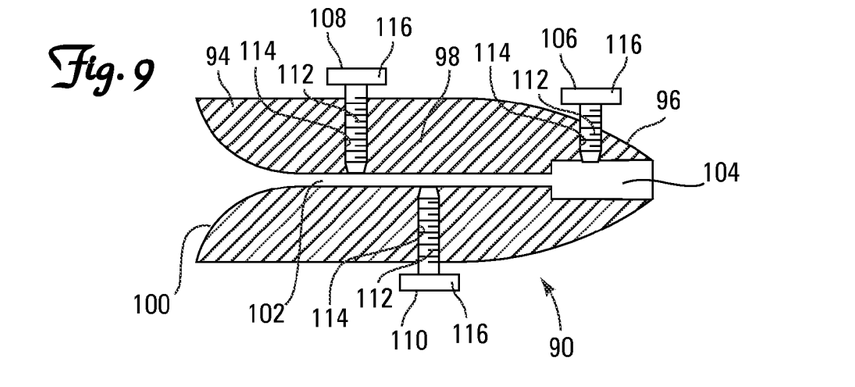
FIG. 9 is a cross-sectional view of the extraction tool of FIG. 8.
Figure 10:
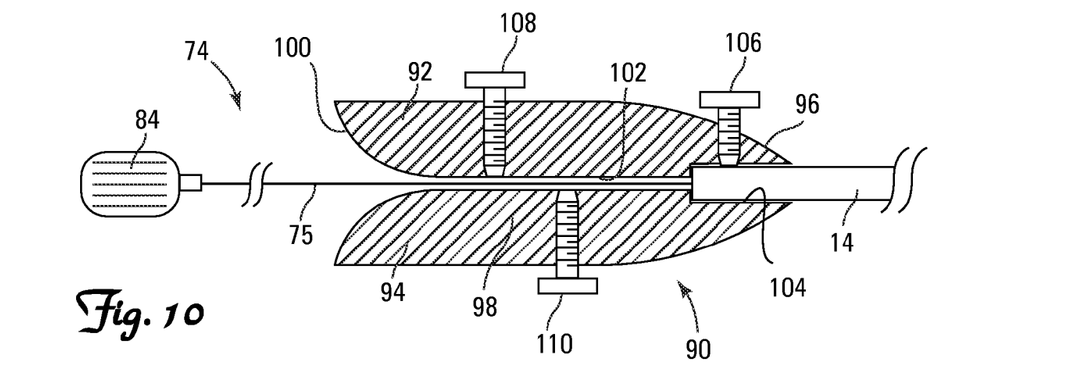
FIG. 10 is a cross-sectional view of the extraction tool of FIG. 8, showing the extraction tool disposed on the lead of FIG. 1 in combination with the extraction stylet of FIG. 6.

In some embodiments, the extraction stylet 74 itself is not sufficient to free the fixation helix 24. FIG. 8 is a side elevation view and FIG. 9 is a cross-section of an extraction tool 90. FIG. 10 is a side elevation view of the extraction tool 90 including the extraction stylet 74 as well as the lead 14.

The extraction tool 90 includes a main body 92 having a proximal section 94, a distal section 96 and an intermediate section 98. As can be seen in FIG. 9, the proximal section 94 includes a funnel 100 that is configured to guide entry of the extraction stylet 74. The funnel 100 narrows to a lumen 102 that extends through the main body 92 to an enlarged opening 104 that is configured to accommodate at least a portion of the connector assembly 40 disposed at a proximal end of the lead 14.

In some embodiments, as illustrated, the extraction tool 90 is configured to be able to selectively and reversibly secure one or more of the terminal pin 48, the extraction stylet 74 and/or the lead 14 relative to the extraction tool 90. In some embodiments, the extraction tool 90 includes a lead locking device 106 that is disposed within the distal section 96 of the extraction tool 90 and that can be moved inward to secure the lead 14 relative to the extraction tool 90. In some embodiments, the extraction tool 90 includes a stylet locking device 108 that is disposed within the intermediate section 98 of the extraction tool 90 and that can be moved inward to secure the extraction stylet 74 relative to the extraction tool 90. In some embodiments, the extraction tool 90 includes a terminal pin locking device 110 that is disposed within the proximal section 94 of the extraction tool 90 and that can be moved inward to secure the terminal pin 48 relative to the extraction tool 90.

In some embodiments, as illustrated, each of the lead locking device 106, the stylet locking device 108 and the terminal pin locking device 110 include a threaded rod 112 that interacts with a corresponding threaded aperture 114 formed within the extraction tool 90 and a knurled thumbwheel 116. Rotating the knurled thumbwheel 116 causes the threaded rod 112 to interact with the threaded aperture 114 and thus move either outwardly to release whichever component is being held or inwardly to secure a desired component, depending on which direction the knurled thumbwheel 116 is rotated.

Figure 11:
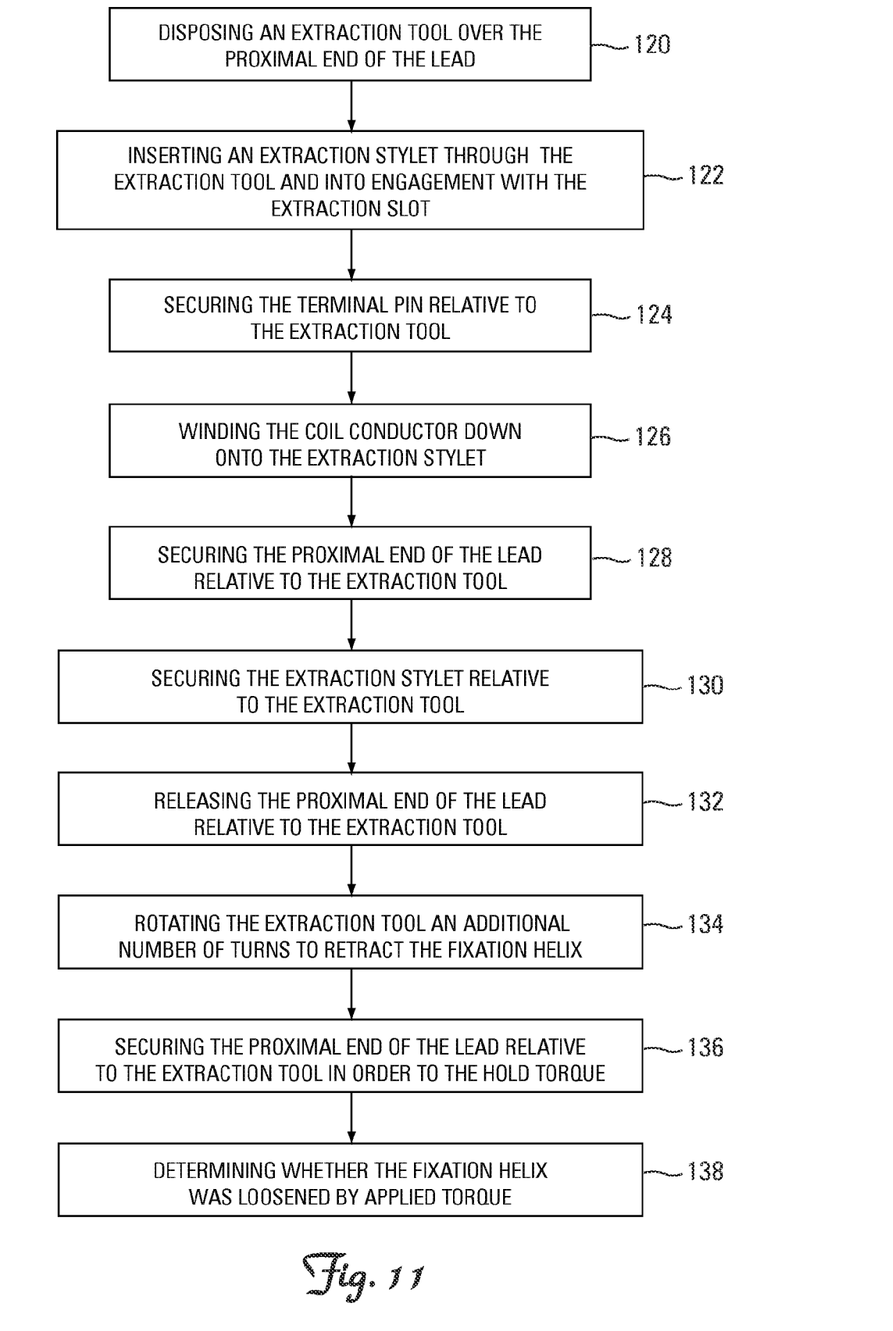
FIG. 11 is a flow diagram illustrating an extraction method using the extraction stylet of FIG. 6 and the extraction tool of FIG. 8.

In some embodiments, the extraction tool 90 facilitates additional extraction techniques. FIG. 11 is a flow diagram providing an illustrative but non-limiting example of an extraction technique that may be carried out using the inventive extraction stylet 74 and extraction tool 90 described herein. When extraction is desired, an extraction tool such as the extraction tool 90 may be disposed over the proximal end of the lead 14, as generally indicated at block 120. As previously discussed, the extraction tool 90 is configured to releasably and interchangeably secure the terminal pin 48, the extraction stylet 74 and/or a proximal end of the lead 14 relative to the extraction tool 90.

An extraction stylet such as the extraction stylet 74 may be inserted through the extraction tool 90 and into engagement with the extraction aperture 72, as seen at block 122. At block 124, the terminal pin 48 may be secured relative to the extraction tool 90 by engaging the terminal pin locking device 110. The conductor coil 64 may be wound down onto the extraction stylet 74 by rotating the extraction tool 90 (and hence the terminal pin 48) a sufficient number of turns to cause the conductor coil 64 to wind down into contact with the extraction stylet 74, as generally indicated at block 126.

In some embodiments, the number of turns may depend, for example, on the outer diameter of the extraction stylet 74 and the inner diameter of the conductor coil 64. In some embodiments, the extraction tool 90 may be rotated about 5 to about 25 turns in order to reduce the inner diameter of the conductor coil 64 until the conductor coil 64 winds down into contact with the extraction stylet 74.

As shown at block 128, the proximal end of the lead 14 may be secured relative to the extraction tool 90 by engaging the lead locking device 106. The extraction stylet 74 may be secured relative to the extraction tool 90 by engaging the stylet locking device 108, as indicated at block 130. At block 132, the lead locking device 106 may be disengaged so that the extraction tool 90 may freely rotate relative to the extraction tool 90.

As shown at block 134, the extraction tool 90 may be rotated an additional number of turns to free and retract the fixation helix 24. Depending for example on the relative diameters of the conductor coil 64 and the extraction stylet 74, the extraction tool 90 may be rotated an additional 5 to about 25 turns, or in some cases about 3 to about 10 turns. Since the conductive coil 64 has been wound down onto the extraction stylet 74, and the terminal pin 48 and the extraction stylet 74 are both secured relative to the extraction tool 90, rotating the extraction tool 90 causes the conductive coil 64 and the extraction stylet 74 to rotate in unison as a unitary structure with increased torque transfer ability.

In some embodiments, if this is not sufficient to break the fixation helix 24 loose, the proximal end of the lead 14 may once again be secured relative to the extraction tool 90 by reengaging the lead locking device 106, as optionally shown at block 136. In some embodiments, additional time with the applied torque is sufficient to break the fixation helix 24 loose, as indicated at block 138. In some embodiments, the extraction tool 90 may be clipped to a surgical drape while waiting for the held torque to loosen the fixation helix 24.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An extraction tool assembly for use with an implantable active fixation lead having a proximal end, a rotatable terminal pin extending from the proximal end, a stylet lumen extending through the terminal pin, and a rotatable active fixation helix coupled an electrode base and to the terminal pin, the extraction tool assembly comprising:
   an extraction stylet flexible for insertion into a body lumen, the extraction stylet including a widened blade portion complementary to an extraction slot disposed within a proximal end of the electrode base; and
   an extraction tool including:
      a main body having a proximal section, a distal section and an intermediate section, a lumen extending through the main body, the lumen configured to accommodate an extraction stylet;
      a funnel formed within the proximal section configured to provide stylet access to the lumen extending through the main body;
      an opening formed within the distal section configured to frictionally engage a proximal end of the implantable lead, the opening aligned with the lumen extending through the main body;
      a lead locking device disposed within the distal section, the lead locking device configured to releasably secure the proximal end of the implantable lead relative to the extraction tool;
      a terminal pin locking device disposed within the intermediate section, the terminal pin locking device configured to releasably secure the terminal pin relative to the extraction tool; and
      a stylet locking device disposed within the proximal section, the stylet locking device configured to releasably secure the extraction stylet relative to the extraction tool.

2. The extraction tool assembly of claim 1, wherein the lead locking device is threadedly engaged with the extraction tool and includes a thumbwheel for rotating the lead locking device between a retracted position in which the lead is movable relative to the extraction tool and an extended position in which the lead is held secure relative to the extraction tool.

3. The extraction tool assembly of claim 1, wherein the terminal pin locking device is threadedly engaged with the extraction tool and includes a thumbwheel for rotating the terminal pin locking device between a retracted position in which the terminal pin is rotatable relative to the extraction tool and an extended position in which the terminal pin is held secure relative to the extraction tool.

4. The extraction tool assembly of claim 1, wherein the stylet locking device is threadedly engaged with the extraction tool and includes a thumbwheel for rotating the stylet locking device between a retracted position in which the stylet is movable relative to the extraction tool and an extended position in which the stylet is held secure relative to the extraction tool.

5. The extraction tool assembly of claim 1, wherein the extraction stylet includes a distal end that is configured to engage an electrode base within the implantable active fixation lead.

6. The extraction tool assembly of claim 5, wherein the electrode base includes an extraction slot disposed within a proximal end of the electrode base, and the distal end of the extraction stylet includes a widened blade portion complementary to the extraction slot.

7. A method of extracting an active fixation lead having a proximal end, a coil conductor, a rotatable terminal pin secured to a proximal end of the coil conductor, a rotatable electrode base secured to a distal end of the coil conductor, the electrode base including an extraction slot, and a fixation helix secured to the electrode base, the coil conductor including a lumen configured to accommodate an extraction stylet, the method comprising steps of:
    disposing an extraction tool over the proximal end of the lead, the extraction tool configured to releasably and interchangeably secure the terminal pin, the extraction stylet and/or a proximal end of the lead relative to the extraction tool;
    inserting an extraction stylet through the extraction tool and into engagement with the extraction slot;
    securing the terminal pin relative to the extraction tool;
    rotating the extraction tool a number of turns sufficient to cause the coil conductor to wind down onto the extraction stylet;
    securing the proximal end of the lead relative to the extraction tool;
    securing the extraction stylet relative to the extraction tool;
    releasing the proximal end of the lead relative to the extraction tool; and
    rotating the extraction tool an additional number of turns to retract the fixation helix.

8. The method of claim 7, further comprising a subsequent step of securing the proximal end of the lead relative to the extraction tool in order to hold any torque previously applied to the extraction stylet and coil conductor.

9. The method of claim 8, further comprising a subsequent step of clipping the extraction tool to a surgical drape to see if the held torque will loosen the fixation helix.

10. The method of claim 7, wherein rotating the extraction tool a number of turns sufficient to cause the coil conductor to wind down onto the extraction stylet comprises rotating the extraction tool about 5 to about 25 turns.

11. The method of claim 7, wherein rotating the extraction tool an additional number of turns to retract the fixation helix comprises rotating the extraction tool about 3 to about 10 turns.

* * * * *